US00PP11528P

United States Patent [19]

Twomey

[11] Patent Number: Plant 11,528

[45] Date of Patent: Sep. 26, 2000

[54] HYBRID TEA ROSE PLANT NAMED 'TWOYEL'

[76] Inventor: Jerry F. Twomey, 194 Avocado St., Leucadia, Calif. 92024

[21] Appl. No.: 09/220,903

[22] Filed: Dec. 24, 1998

[51] Int. Cl.[7] ..... A01H 5/00

[52] U.S. Cl. ..... Plt./134

[58] Field of Search ..... Plt./134, 135, 145, Plt./146

*Primary Examiner*—Howard J. Locker

[57] ABSTRACT

A new rose cultivar of the Hybrid Tea class characterized by having deep, pure non-fading yellow flowers with a strong persistent spicy fragrance on a very upright plant. This plant has been designated as 'TVOYEL'. It is being marketed in the USA under the tradename of 'Dream Yellow'.

1 Drawing Sheet

The present invention relates to a new and distinctive cultivar of rose plant of the Hybrid Tea class, which was originated by my crossing an unnamed seedling ('Sonia×Prominent') as the seed parent with the pollen parent 'Whisky Mac'.

Among the novel characteristics possessed by the new cultivar which distinguish it from:

(a) All other cultivars of which I am aware are: (1) Excellent non-fading pure yellow flowers. (2) Very strong spicy fragrance. (3) Free blooming with very fast repeat. (4) Roots readily on its own wood.

(b)

*Seed parent*.—Pale yellow flower, hybrid Tea,

*Pollen parent*.—Yellow/orange flower, hybrid Tea.

Asexual reproduction of the new rose cultivar by budding, as performed at Wasco, Calif. shows that the aforementioned and all other distinctive characteristics come true to form and are established and transmitted through succeeding propagations.

The accompanying drawing shows typical specimens of the vegetative growth and flowers of the new cultivar in different stages of development and as depicted in color as nearly true as it is reasonably possible to make the same in a color illustration of this character.

The following is a detailed description of my new cultivar, with color terminology in accordance with The Royal Horticultural Society Colour Chart (R.H.S.C.C.). The terminology used in the color description herein refers to plate numbers in the aforementioned color chart, e.g. "53A" is plate "53A" of The Royal Horticultural Society Colour Chart.

Parentage:

*Seed parent*.—Unnamed seedling ('Sonia'× 'Prominent').

*Pollen parent*.—'Whiskey Mac', not patented.

Class: Hybrid Tea

The following observations are made of specimens grown outdoors in Monterey, Calif. in the month of September, 1998.

FLOWER

Blooming habit:

A. Bud:

(1) *Size*.—Sepals enclosed, 19–21 mm from base of sepals to top of bud.

(2) *Form*.—Ovoid.

(3) *Sepals*.—26 to 28 mm in length; 6 to 7 mm extension beyond bud; no serration shown on sepal edges. Generally 3 out of 5 sepals show appendages on each side, 3 to 6 mm length. Sepals show glandular development on edges. fine cotton matting on inner surface, Outside color — 148A; inside — 148D.

(4) *Peduncle*.—Length — 35 to 40 mm. Surface — smooth, no prickles, a few glandular hairs. Strength — firm. Color — 138B, shaded — 178A.

(5) *Receptacle*.—Shape — cupped, 18–20 mm diameter. Color — 148A.

(6) *Color*. — When sepals first divide, outside bud petals near to 13A.

B. Bloom:

(1) *Size*.—When open — 10 to 12 cm.

(2) *Borne*.—Cluster — 6–12 per stem.

(3) *Form*.—Cupped.

(4) *Petalage*.—Average — 36 to 40.

(5) *Color*.—Early open: outer petals near 16A (both surfaces); inner petals near 16B (both surfaces). Aging: near 16C.

C. Petals:

(1) *Texture*.—Average.

(2) *Appearance*.—Rich, buttery yellow.

(3) *Form*.—Slight ruffle on edge.

(4) *Arrangement*.—Symmetrical, somewhat loose.

(5) *Petaloids in center*.—Average 3–5.

(6) *Persistence*.—Petals persist.

(7) *Fragrance*.—Strong spicy.

(8) *Lasting quality*.—On plant 6–7 days; cut 5–6 days.

REPRODUCTIVE ORGANS

A. Stamen:

(1) *Arrangement*.—Regular around styles.

(2) *Number*.—Average 135–145.

(3) *Length*.—Average — 6 to 8 mm.

(4) *Filaments*.—Color — Close to 13B.

(5) *Anthers*.—Color — Close to 23C.

(6) *Pollen*.—Color — Close to 23C.

B. Pistil:

(1) *Styles*.—Length: 3–4 mm exposed; number: 135 to 145; color: near to 154C; sparsely coated with white hairs.

(2) *Stigma*.—Color — Close to 42A.

(3) *Ovary*.—Shape — Cupped; 8–9 mm center cross-section at sepal base.

C. Hips: Color: 35A with shades of 42B. Diameter: 22–24 mm. Seeds: 10 to 12.

PLANT

A. Form: Upright.
B. Growth: Vigorous. Height: average 1–1⅓ m.
C. Stem length: Basal break to flower bud tip: average — 1 m.
D. Foliage: Compound of 3 to 5 leaflets on bloom stem; 5 to 7 leaflets on main canes.
(1) *Mature size*.—5 leaflet — tip of leaflet to stipule base 14–15 cm.
(2) *Quantity*.—Stems well covered.
(3) *Color*.—New foliage upper side close to 146A; under side near 146B. Old foliage upper side near to 147A, under side near to 147B.
(4) *Shape*.—Oval with center pointed.
(5) *Texture*.—Firm, leathery, slightly glossy.
(6) *Edge*.—Slight serration on outer edge. Average 3–4 points per 1 cm, with up to 1 mm peak.
(7) *Rachis*.—Glandular hair on upper side; lower side none; 3–4 prickles on lower side: 1–3 mm length, hooked, 3 cm spacing.
(8) *Stipules*.—Length 2½ cm; auricle to 6–7 mm. Edge of stipule to tip of auricle with many glandular hairs.
E. Resistance to disease: Powdery mildew and blackspot — fair; rust good.
F. Wood:
*New wood*.—Color close to 146B; Bark — smooth.
*Old wood*.—Color close to 147B; Bark — smooth.
G. Thorns on mature wood:
*Size*.—9–11 mm.
*Number per* 10 cm.—Primary wood 8–l0 thorns; Secondary wood same.
*Shape*.—Very pointed, almost 90 degree from base.
*Color*.—Close to 139B.
H. Winter hardness: Average.

I claim:

1. A new and distinct rose cultivar of the hybrid tea class, substantially as herein shown and described.

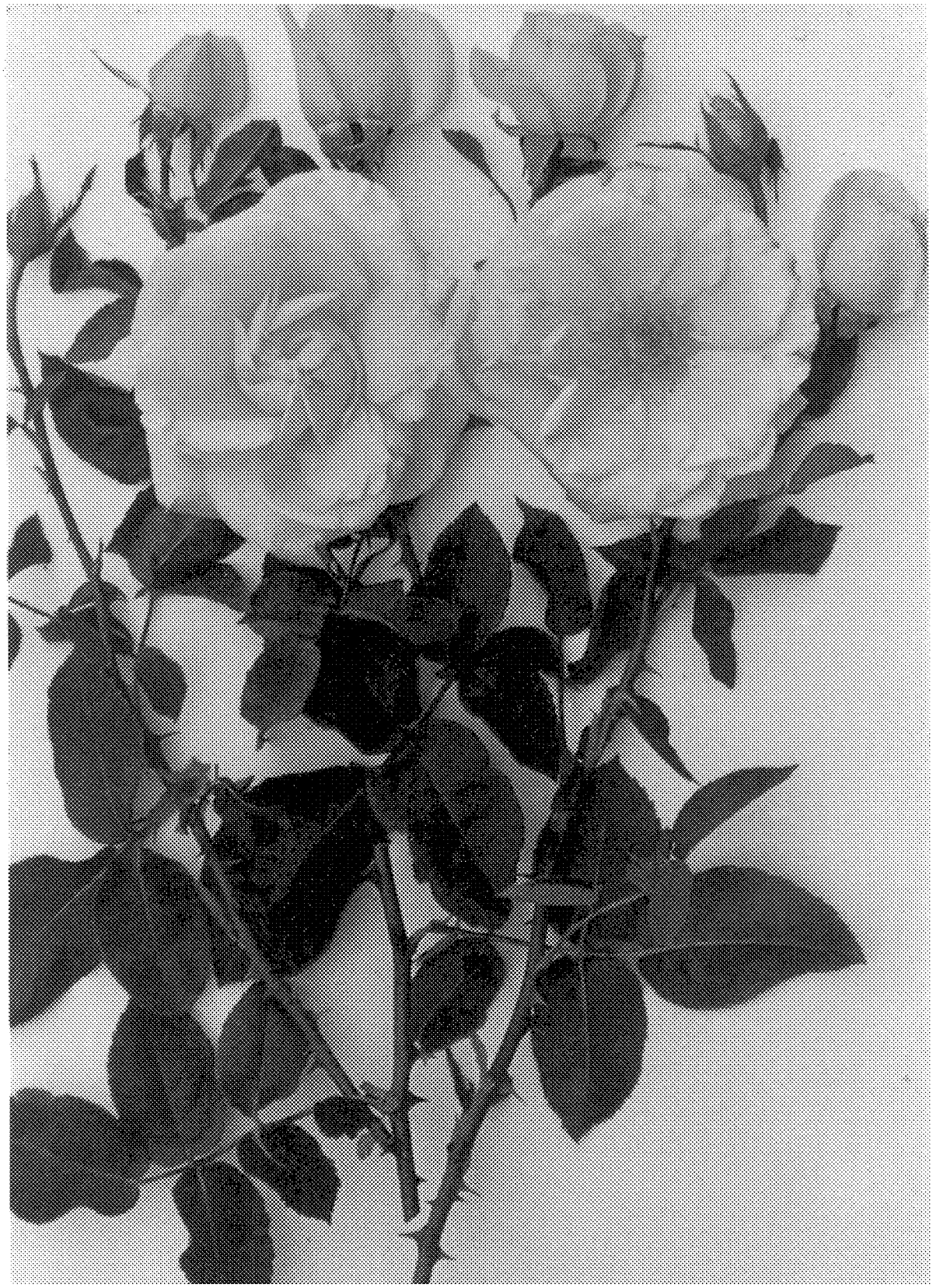

* * * * *